(12) United States Patent
Li

(10) Patent No.: US 6,268,511 B1
(45) Date of Patent: Jul. 31, 2001

(54) ITACONATE DERIVATIVES USED FOR A COMPONENT OF A POLYMER

(75) Inventor: Fumian Li, 47-108 Zhongguanyuan, Haidian District, Beijing 100871 (CN)

(73) Assignees: Santen Pharmaceutical Co., Ltd., Osaka (JP); Fumian Li, Beijing (CN)

( * ) Notice: Subject to any disclaimer, the term of this patent is extended or adjusted under 35 U.S.C. 154(b) by 0 days.

(21) Appl. No.: 09/445,282

(22) PCT Filed: Jun. 5, 1998

(86) PCT No.: PCT/CN98/00095

§ 371 Date: Dec. 3, 1999

§ 102(e) Date: Dec. 3, 1999

(87) PCT Pub. No.: WO98/55444

PCT Pub. Date: Dec. 10, 1998

(30) Foreign Application Priority Data

Jun. 5, 1997 (CN) .................................. 97112170

(51) Int. Cl.[7] ...................... C07C 69/593; C07D 207/27; C08F 220/10; C08F 222/10; C02B 1/04
(52) U.S. Cl. ........................ 548/530; 523/108; 526/264
(58) Field of Search .......................... 548/530; 523/108; 526/264

(56) References Cited

U.S. PATENT DOCUMENTS

| 4,123,407 | 10/1978 | Gordon . |
| 4,956,432 | 9/1990 | Vacik et al. . |

FOREIGN PATENT DOCUMENTS

| 30250/89 | 8/1989 | (AU) . |
| 1152584 | 6/1997 | (CN) . |
| 0 072 067 | 2/1983 | (EP) . |
| 0072067 A1 | 2/1983 | (EP) . |
| 0 869 138 | 10/1998 | (EP) . |
| 53-105250 | 9/1978 | (JP) . |
| 2-8218 | 1/1990 | (JP) . |
| 2-43208 | 2/1990 | (JP) . |
| 4-28705 | 1/1992 | (JP) . |
| 5-080279 | 4/1993 | (JP) . |
| 5-80279 | 4/1993 | (JP) . |
| 5-150197 | 6/1993 | (JP) . |
| 6-123862 | 5/1994 | (JP) . |

OTHER PUBLICATIONS

Database Chemabs Online!, Chemical Abstracts Service, Pan, Huaizhong et al: "Synthesis and properties of itaconate polymers having pyrrolidinonyl moiety and homopolymers thereof", Database accession No. 129:109369, Gaofenzi Xuebao (1998), (3), 381–384.

Database Chemabs Online!, Chemical Abstracts Service, Pan, Huaizhong et al: "Thermo–responsive behavior of polymer and hydrogels based on itaconate having pyrrolidinonyl moiety", Database accession No. 129:276786, Gaofenzi Xuebao (1998), (4), 490–493.

*Primary Examiner*—Paul R. Michl
(74) *Attorney, Agent, or Firm*—Frishauf, Holtz, Goodman, Langer & Chick, P.C.

(57) ABSTRACT

An itaconic acid derivative having the following formulas (1) or (2):

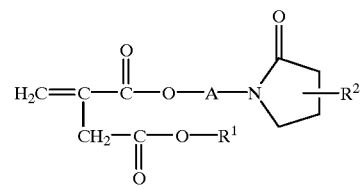

(1)

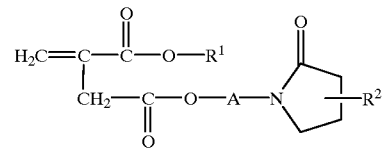

(2)

wherein $R^1$ represents a hydrogen atom, a lower alkyl group or a phenyl lower alkyl group, wherein the phenyl ring of the phenyl lower alkyl group is unsubstituted or substituted by at least one lower alkyl group, $R^2$ represents a hydrogen atom or a lower alkyl group and A represents a lower alkylene group, or salts thereof. Copolymers can be made from the itaconic acid derivatives.

39 Claims, No Drawings

ITACONATE DERIVATIVES USED FOR A COMPONENT OF A POLYMER

CROSS REFERENCE TO RELATED APPLICATION

This application is a U.S. National Phase Application Under 35 USC 371 of International Application PCT/CN98/00095 filed Jun. 5, 1998 (not published in English).

BACKGROUND OF THE INVENTION

1. Field of the Invention

The present invention provides a novel itaconic acid derivative which is useful as a constituting component of a polymer, and also provides a copolymer containing the novel itaconic acid derivative as a constituting component, and an intraocular lens formed from the copolymer, particularly a foldable intraocular lens which can be implanted into eyes in the state of being folded (hereinafter abbreviated as "foldable IOL").

2. Background Information

A number of studies on an acrylic acid monomer as a constituting component of a polymer have been made. However, there have not been so many studies made on the use of an itaconic acid derivative having two carboxyl groups as a monomer. The itaconic acid derivative of the present invention, which is represented by the general formula [1] or [2] and is useful as a polymer component, has such a structural feature that a pyrrolidone group is contained. The itaconic acid derivative having such a feature is a compound which is unknown in the literature as a monomer. As a matter of course, a polymer containing the monomer as a constituting component is also unknown in the literature.

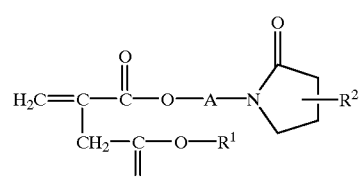

[1]

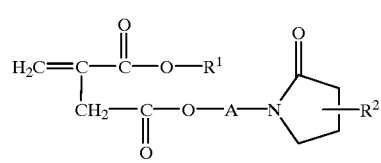

[2]

A main object of the present invention is to prepare a novel polymer containing the above-described itaconic acid derivative as a constituting component and to develop a novel material to be applied to intraocular lenses, particularly foldable intraocular lenses.

An intraocular lens (IOL) is used for implanting in place of a crystalline lens removed on cataract surgery. Since IOL was first used in transplanting in 1949, various studies have been made on IOL materials. As there is a great evolution on operation methods, with the advancement of operation methods, demands on the characteristics of IOL have also changed a lot. Recently, with the popularity of the phacoemulsification procedure etc., it is possible to open a very small incision to remove the opaque crystalline lens and finish the operation. Accordingly, demands on characteristics of IOL to be implanted have been changing. For example, characteristics of so-called foldable IOL make it possible to implant an IOL through the small incision in foldable form and open an IOL in lens the capsule. At the same time, various studies have been made on IOL materials. Polymethyl methacrylate (PMA), Silicone, acrylic resin or the like have widely been used an the IOL materials heretofore, while silicone or acrylic resin can be used as foldable IOL materials. A Copolymer of hydroxyethyl methacrylate and methyl methacrylate may also have been used recently. On the other hand, during the studies on these kinds of materials in order to prevent the effect of UV rays on the retina, they can contain an UV absorber such as hydroxybenzophenone, hydroxyphenyl benzotriazole and so on. Moreover, in order to raise biocompatiability and prevent deposition of cells, a polysaccharide such as heparin in coated on the IOL surface in practice.

The itaconic acid derivative of the present invention is characterized by having a pyrrolidone group, and there has been no report on a polymer made up of the itaconic acid derivative. Paying attention to polymers containing a monomer having a pyrrolidone group as a constituting component, particularly polymers used for the purpose of being applied to an intraocular lens, some prior arts are shown below for reference. These prior arts relate to the polymers whose partial constituting component is an acrylic monomer having a pyrrolidone group. Examples of such polymers are a copolymer of methacryloyloxyethyl-2-pyrrolidone and acrylic acid (JP Laid-Open 28705/1992), a polymer polymerized from the monomer which is formed from amidation of acrylic acid and pyrrolidone (JP Laid-Open 43208/1990). a polymer of polyoxyalkylene structure a with pyrrolidone group (JP Laid-open 8218/1990) and so on. As for copolymers formed form three components, there have been reports only an a copolymer of vinyl pyrrolidone, hydroxyethyl methacrylic acid and methyl methacrylate (JP Laid-Open 105250/1978), and a copolymer of methacryloyloxy ethyl-2-pyrrolidone, alkyl methacrylate and fluoroalkyl methacrylate (JP Laid-Open 150197/1993). Incidentally, the main object of these studies is the application on a soft contact lens and not on an IOL. There have been no report especially on the possibility of application of a foldable IOL in the present invention.

A main object of the present invention is to develop an intraocular lens, more particularly materials of a foldable IOL. During the studies on foldable IOL materials, it is necessary to consider refractive index, tensile strength and recovery speed of the materials. For example:

1) When the refractive index is too low the thickness of IOL increases too much. Contrarily when the refractive index is too high, the aberration of peripheral portion becomes large. Accordingly, it is necessary to choose proper refractive index. Specifically, the preferable range is 1.4–1.6.

2) Because forceps are used to implant a foldable IOL, tensile strength bearing their operation is needed. It is an important factor that marks do not remain on the IOL surface after the operation with the forceps.

3) After foldable IOL are implanted, they must be recovered to thee original form in the lens capsule. Recovering speeds vary depending on an operator's custom and competence. The possibility of mechanical invasion of peripheral tissue usually increases with the acceleration of recovering speed. On the other hand, with the slowdown of recovering speed and the elongation of an operation, the possibility of mechanical invasion of peripheral tissue increases. Accordingly, for the foldable IOL, suitable recovering speed is needed.

Moreover, easy formability should be taken into consideration.

Based on these opinions, though various foldable IOL have been used in practice, it is desired to develop an more preferable material.

SUMMARY OF THE INVENTION

The Inventor, with the consideration of the above problems, studied on more applicable materials of foldable IOL. First, the inventor has focused attention and studied on itaconic acid having two carboxyl groups, capable of synthesizing various derivatives, and succeeded in the preparation of a series of novel itaconic acid derivatives having a pyrrolidone group. Itaconic acid is an very useful compound capable of being converted into various derivatives according to purposes because of two carboxyl groups as described above. As a result of studies on preparation of various polymers using the itaconic acid derivative as one of monomers, the inventor found that the itaconic acid derivative can be suitably used as the monomer and that the resulting polymer, particularly a copolymer with an hydroxyalkyl acrylate derivative and an alkyl acrylate derivative can be used as the material of particularly excellent foldable IOL.

The present invention is composed of the following four constituent features:

(1) A novel itaconic acid derivative represented by the following general formula [1] or [2]:

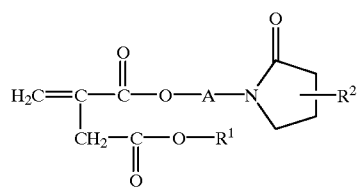

[1]

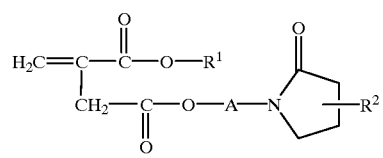

[2]

[wherein $R^1$ represents hydrogen atom, lower alkyl group or phenyl lower alkyl group, and phenyl ring of the phenyl lower alkyl group can be substituted by lower alkyl group (s); $R^2$ represents hydrogen atom or lower alkyl group; and "A" represents lower alkylene group; the same rule applies correspondingly to the following] which is useful as a polymer constituting component, or a salt thereof;

(2) Use of the novel itaconic acid derivative represented by the general formula [1] or [2] as a polymer constituting component;

(3) A copolymer comprising constituent units represented by the following formulas [3] and, [4] or [5], and [6]:

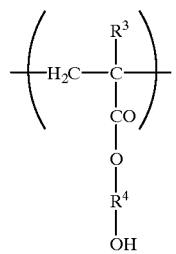

[3]

[wherein $R^3$ represents hydrogen atom or lower alkyl group; $R^4$ represents lower alkylene group, and the alkylene group can be substituted by hydroxy group(s) and can have oxygen atom(s) in the alkylene chain];

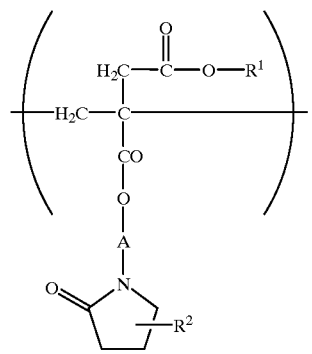

[4]

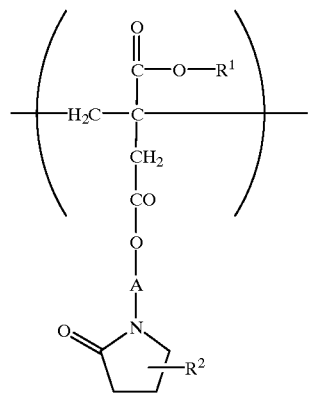

[5]

[wherein $R^1$ represents hydrogen atom, lower alkyl group or phenyl lower alkyl group, and phenyl ring of the phenyl lower alkyl group can be substituted by lower alkyl group (s); $R^2$ represents hydrogen atom or lower alkyl group; and "A" represents lower alkylene group; the same rule applies correspondingly to the following]; and

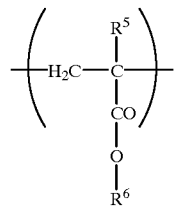

[6]

[wherein $R^5$ represents hydrogen atom or lower alkyl group; and $R^6$ represents lower alkyl group; the same rule applies correspondingly to the following];

(4) An intraocular lens produced by forming from the above copolymer, particularly a foldable intraocular lens.

DETAILED DESCRIPTION OF THE INVENTION

In the present invention, the lower alkyl means a straight-chain or branched alkyl having 1 to 6 carbon atoms, such as methyl, ethyl, propyl, isopropyl, butyl, isobutyl, hexyl or the like, and the lower alkylene means a straight-chain or branched alkylene having 1 to 6 carbon atoms, such as $-CH_2-$, $-(CH_2)_2-$, $-(CH_2)_3-$, $-C(CH_3)_2-$, $-(CH_2)_4-$ or $-(CH_2)_6-$.

Each constitution feature is described in detail below.

(1) A typical synthesis method of the novel itaconic acid derivative represented by the general formula [1] or [2] is shown in the following (a) to (d).

(a)

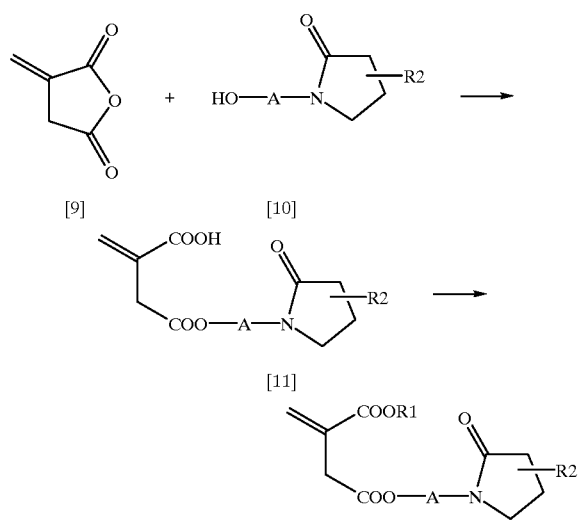

this method is a method of reacting itaconic anhydride [9] with a pyrrolidone derivative [10] to obtain a monoester [11]. If necessary, the monoester can also be converted into a diester by reacting it with an esterifying agent such as dimethyl sulfate.

(b)

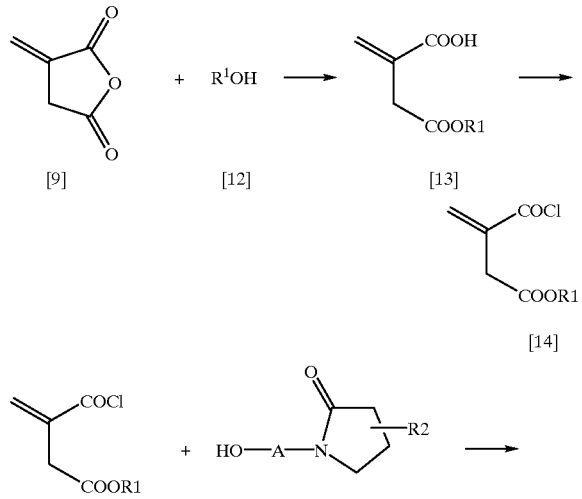

This method is a method of reacting itaconic anhydride with alcohol [12] to obtain a monoester [13], converting it into an acid chloride [14] using thionyl chloride or the like, and reacting it with a pyrrolidone derivative [10] to obtain a diester. The diester can be optionally converted into a desired monoester by partial hydrolysis using a conventional method.

(c)

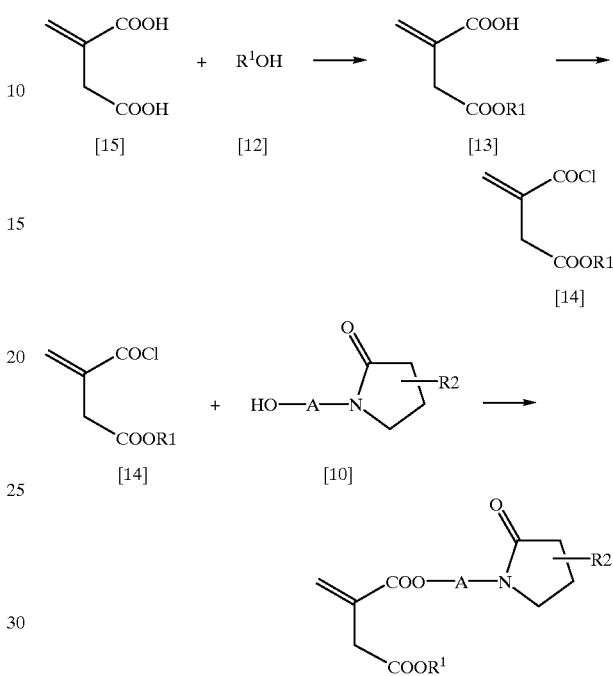

This method is a method of reacting itaconic acid [15] with an alcohol [12] to obtain a monoester [13], and converting it into a diester in the same manner as in method (b).

(d)

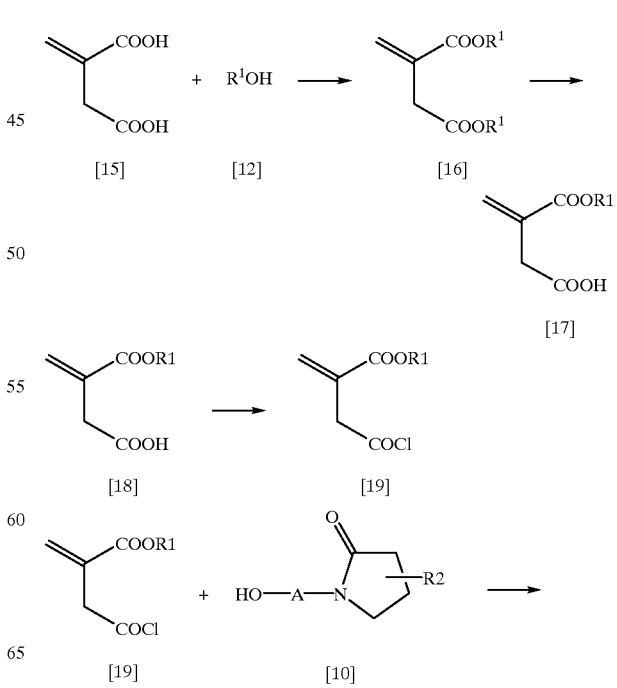

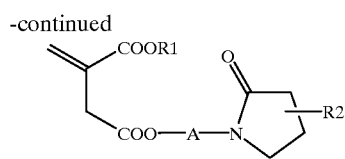

This method is a method of synthesizing a diester [16], heating the diester, for example, in formic acid in the presence of paratoluenesulfonic acid to obtain a monoester [18], and converting it into a diester in the same manner as in method (b).

Preferred examples of the respective groups defined above are as follows. That is, $R^1$ is preferably a methyl group, propyl group, butyl group, phenylmethyl group, or phenylethyl group. $R^2$ is preferably a hydrogen atom. "A" is preferably —(CH$_2$)$_2$—. A Preferred combination of groups is the combination of the above-described atom and groups. Particularly preferred compounds are exemplified by the following compounds.

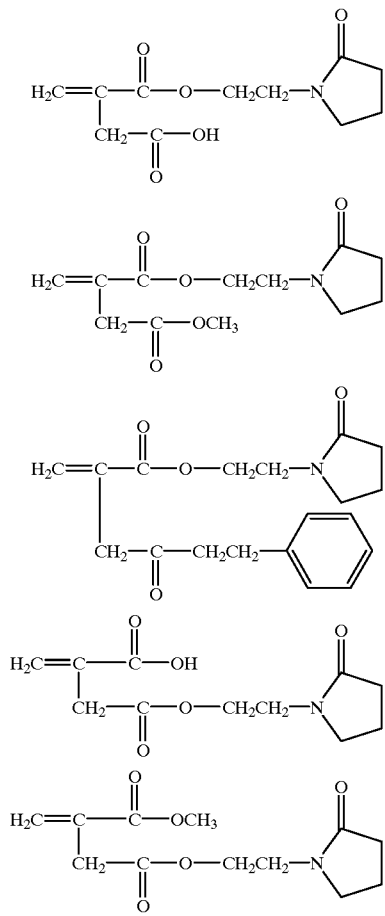

(2) The above-described novel itaconic acid derivative is suitably used as the constituting component of the polymer as shown in the following (3) and (4), and a copolymer with an acrylic acid monomer is particularly preferred as the raw material of a foldable IOL.

(3) Regarding the weight ratio of the copolymer comprising constituent units represented by the general formulas [3] and, [4] or [5], and [6], the weight ratio of the constituent unit [3] is within a range from 60 to 80, that of the constituent unit [4] or [5] is from 10 to 30, and that of the constituent unit [6] is from 5 to 20. The weight ratio of the constituent unit [3] is preferably within a range from 65 to 75, that of the constituent unit [4] or [5] is preferably from 15 to 25, and that of the constituent unit [6] is preferably from 5 to 15. The weight ratio of the constituent unit [3] is particularly preferably 70, that of the constituent unit [4] or [5] is particularly preferably 20, and that of the constituent unit [6] is particularly preferably 10.

The copolymer is represented by the repeating unit as follows.

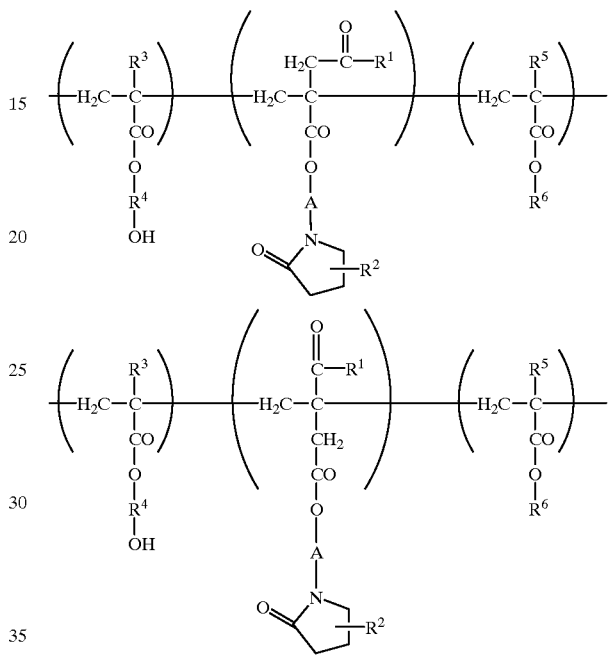

Preferred examples of the respective groups defined above are as follows. That is, $R^3$ is hydrogen atom or methyl group, $R^4$ is —(CH$_2$)$_2$—, $R^1$ is a hydrogen atom, a methyl group, propyl group, butyl group, phenylmethyl group or phenylethyl group, $R^3$ is a hydrogen atom, A is —(CH$_2$)$_2$—, $R^5$ is hydrogen atom or a methyl group, and $R^6$ is a methyl group. A preferred combination of groups is the combination of the above-described atom and groups. A particularly preferred combination is that wherein $R^3$ is a methyl group, $R^4$ is —(CH$_2$)$_2$—, $R^1$ is a hydrogen atom, methyl group or phenylethyl group, $R^2$ is a hydrogen atom, A is —(CH$_2$)$_2$—, $R^5$ is a methyl group, and $R^6$ is a methyl group.

The copolymer can be well produced by mixing the respective monomer components and adding potassium persulfate, ammonium persulfate, benzophenone or methacryloyloxyhydroxybenzophenone as a polymerization initiator.

Generally, azodiisobutyronitrile is most widely used as a polymerization initiator in copolymer the synthesis, but when it is used in synthesis of a foldable IOL material which is a purpose of the present invention, mechanical strength of the material is not satisfactory. The inventor precisely studied on polymerization initiators and found that when potassium persulfate, ammonium persulfate, benzophenone or methacryloyloxy hydroxybenzophenone used as a polymerization initiator, a copolymer with satisfactory mechanical strength for a material of a foldable IOL can be obtained.

On the other hand, the molecular weight (viscosity-average molecular weight) of the copolymer of the present invention can be 10,000 or more. Generally, the molecular weight has no great effect on characteristics of the copolymers, and it is not an important factor, but it has an effect on the strength of the copolymers. The relation between the molecular weight and strength of the copolymers is about a linear proportional relation when the molecular weight is about 10,000 or less, but when the molecular weight is higher than 10,000, the strength of the copolymers reaches about a maximum value and becomes close to a constant value. Accordingly, when the molecular weight is lower than 10,000; the strength of the copolymers is not stable and it is likely to cause problems when the copolymers are used as a foldable IOL, but when the molecular weight in higher than 10,000, problems scarcely arise. However, if the molecular weight is too high, the strength of the copolymers used as a foldable IOL is not preferable. Accordingly, the preferable range of the molecular weight of the copolymers is from 10,000 to 100,000. The molecular weight of the copolymers in the following examples is also within this range.

(4) In accordance with the constitution of the present invention, by selecting properly the ratio of each component, refractive index, surface tensile strength, and recovering speed can be adjusted according to needs. For example, an increase in the ratio of component [3] scarcely influences the refractive index and the recovering speed, but tend to slightly decrease the tensile strength. An increase in the ratio of component [4] or [5] leads to the effect of increasing the refractive index and hardly influences the recovering speed, but tends to slightly reduce the tensile strength. An increase in the ratio of component [6] leads to an increase in the recovering speed and the tensile strength, but tends to slightly reduce the refractive index. By satisfactorily utilizing these characteristics, the desired foldable IOL can be obtained. The preferred ratio of each component is the same as described above. When the preferred component ratio is used, a refractive index is 1.4–1.6, a recovering speed is not too fast or too slow, i.e. 3–6 seconds, and a tensile strength is just the one which could fully bear forceps operation, that is to say, after implantation in eyes (being swollen-wetted), a foldable IOL with a tensile strength being 10 psi or over could be obtained. Marks do not remain on the IOL produced by forming from the copolymer of the present invention even after the operation with the forceps.

Recovering speed could be adjusted to be 3–6 seconds with 2 seconds variation amplitude because it varies depending on operator's custom as described above.

There are hydrophilic and hydrophobic foldable IOL, and they are used respectively according to purpose. The copolymers of the present invention are hydrophilic. A Hydrophilic foldable IOL would be transported and stored under dry condition. Before utilization, being swollen and wetted with purified water, a foldable IOL are implanted in eyes. It is possible to assume hydrophilicity in accordance with the rate of water content. Hydrophilicity has an effect on biocompatibility and flexibility of a foldable IOL. Under the circumstances of the present invention, it is possible to choose the water content by selecting a ratio of each component. For example, an increase in the ratio of component [3] and an increase in the ratio of component [4] or [5] increase the water content, while an increase in the ratio of component [6] decreases the water content. The water content is preferably from 25 to 50%.

The copolymers of the present invention can be intramolecular crosslinked. Physical strength and water content can be adjusted by crosslinking. Bisacrylate compounds or bisacrylamide compounds can be used as a crosslinking agent, for example, ethylene glycol bismethacrylate, diethylene glycol bismethacrylate or N,N'-methylene bisacrylamide. Wen the amount of the crosslinking agent is too large, the copolymers would become hard and the recovering speed would become fast, however, the copolymers become brittle. The range of the crosslinking agent content is 0.01–2.0 wt %, preferably 0.1–1.0 wt % based on the polymer weight.

UV absorbers are widely used in an IOL in order to prevent the harmful effect on the retina, and the copolymers of the present invention can also contain an UV absorber to some extents. There are two methods to incorporate an UV absorber, that is, incorporating an UV absorber by physical method (this method is widely used in practice) and combining an UV absorber with the copolymers with chemical method (an UV absorber itself functions as a monomer component constituting the polymer). In the present invention, both methods can be used. Especially in the chemical method, there is an advantage that an UV absorber does not blood out from the IOL when the IOL is used. There is no special limits on the varieties of UV absorbers, so long as they are used in an IOL. For example, benzophenone compounds, benzotriazole compounds or acrylic acid derivatives thereof, specifically, hydroxybenzophenone, hydroxybenzotriazole or acrylic acid derivatives thereof such as 4-methacryloyloxy-2-hydroxybenzophenone as used as UV absorbers.

In order to raise biocompatibility and prevent deposition of calls, a technique of polysaccharide coating on an IOL surface has been used recently. Because the copolymer of the present invention has a free hydroxyl group at the terminal thereof, it can combine with a polysaccharide by a covalent bond, and problems such as peel of the coatings do not occur. This covalent bond can be formed very easily by treatment using, for example, divinyl sulfone. Specific examples of the polysaccharide are heparin, hyaluronic acid or a salt thereof such as sodium salt or potassium salt.

The present invention provides a flexible IOL material having pliability. After an operation with forceps, marks of forceps remains and it must take some time to recover to its original form. But the problems could be resolved because the copolymers of the present invention have excellent recovering ability.

Furthermore, a laser beam is sometimes used for treating secondary cataract etc. When it becomes necessary to perform such a treatment after implantation of an IOL, a conventional silicone IOL sometimes makes a crystalline lens opaque to impair the transparency. There is also a possibility that slight deformation and cracking occur at the peripheral portion to slightly impair the visual field. However, when the copolymer of the present invention is used, such opacity would not be found and the transparency can be maintained and, furthermore, peripheral deformation or cracking does not occur.

The copolymer of the present invention can be easily formed into a foldable IOL in the form to be used actually. The forming can be conducted by using a known method.

The copolymer of the present invention is particularly suited for an IOL, and properties thereof can also be applied suitably for a soft contact lens.

BEST MODE FOR CARRYING OUT THE INVENTION

EXAMPLE 1

Synthesis of 4-[2-(2-pyrrolidone-1-yl)ethyl] itaconate (PyEI)

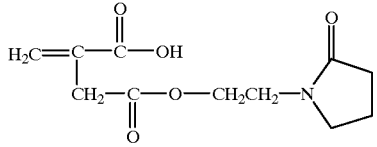

Itaconic anhydride (2.1 g) and 1-(2-hydroxyethyl)-2-pyrrolidone (1 ml) were added to chloroform (10 ml) and the mixture was refluxed for 36 hours. After the reaction solution was cooled, the precipitated solid was filtered off and recrystallized from acetone to obtain 1.5 g of the desired 4-[2-(2-pyrrolidone-1-yl)ethyl]itaconate (PyEI).

Melting point: 100–102° C. MS: 342

In the same manner as in Example 1, the following compounds can be obtained.

4-(2-pyrrolidone-1-ylmethyl)itaconate
4-[3-(2-pyrrolidone-1-yl)propyl)itaconate

EXAMPLE 2

Synthesis of 1-methyl 4-[2-(2-pyrrolidone-1-yl) ethyl]itaconate (MPyEI)

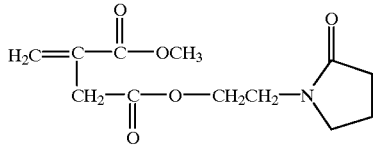

PyEI (0.96 g) was dissolved in an aqueous 10% potassium carbonate solution and dimethylsulfuric acid (0.38 ml) was added thereto dropwise under stirring. After the reaction solution was allowed to stand at room temperature overnight and extracted with ethyl acetate, the organic layer was washed with water, dried over anhydrous sodium sulfate and concentrated under reduced pressure. The resulting oily substance was distilled under reduced pressure to obtain the titled compound (0.50 g).

Boiling point: 140–150° C./0.2 mmHg; $^1$H-NMR ($\delta$, ppm, CDCl$_3$): 6.35 (s, 1H), 5.75 (s, 1H), 4.25 (t, 2H), 3.77 (s, 3H), 3.57 (t, 2H), 3.49 (t, 2H), 3.35 (s, 2H), 2.41 (t, 2H), 2.06 (m, 2H).

In the same manner as in Example 2, the following compounds can be obtained.

1-methyl 4-(2-pyrrolidone-1-ylmethyl)itaconate
1-methyl 4-[3-(2-pyrrolidone-1-yl)propyl)itaconate
1-ethyl 4-[2-(2-pyrrolidone-1-yl)ethyl]itaconate
1-propyl 4-[2-(2-pyrrolidone-1-yl)ethyl)itaconate

EXAMPLE 3

Synthesis of 4-methyl 1-[2-(2-pyrrolidone-1-yl) ethyl)itaconate (4-MPyEI)

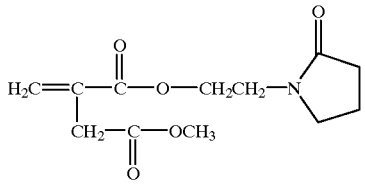

(1) To a methanol (100 ml) solution of itaconic acid (100 g), benzoyl chloride (4 ml) was added dropwise under stirring. The reaction solution was stirred at 60–70° C. for 20 minutes and then concentrated under reduced pressure. The resulting solid was recrystallized from a mixed solution of benzene and petroleum ether to obtain 4-methyl itaconate (93 g, melting point: 65–67° C.).

(2) To an other (23 ml) solution of 4-methyl itaconate (32 g) obtained above, thionyl chloride (23 ml) was added and the mixture was refluxed for 15 minutes. After the reaction solution was concentrated under reduced pressure, the resulting oily substance was distilled under reduced pressure to obtain 4-methyl itaconyl chloride (29 g, boiling point: 68–69° C./2–3 mmHg).

(3) To a benzene (50 ml) solution of 1-(2-hydroxyethyl)-2-pyrrolidone (12.9 g) and triethylamine (10.1 g), 4-methyl itaconyl chloride (16.3 g) obtained above was added dropwise with stirring vigorously under cooling. After the reaction solution was allowed to stand at room temperature overnight, the precipitate was filtered out. The filtrate was washed in turn with 3% hydrochloric acid, an aqueous saturated sodium carbonate solution and a saturated sodium chloride aqueous solution. The organic layer was dried over anhydrous sodium sulfate and then concentrated under reduced pressure. The resulting oily substance was distilled under reduced pressure to obtain 7.7 g of the desired 4-methyl 1-[2-(2-pyrrolidone-1-yl)ethyl]itaconate (4-MPyEI).

Boiling point: 140–150° C./0.2 mmHg;

$^1$H-NMR ($\delta$, ppm, CDCl$_3$): 6.34 (s, 1H), 5.76 (s, 1H), 4.31 (t, 2H), 3.70 (s, 2H), 3.60 (t, 2H), 3.48 (t, 2H), 3.35 (s, 2H), 2.39 (t, 2H), 2.05 (m, 2H).

In the same manner as in Example 3, the following compounds can be obtained.

4-methyl 1-(2-pyrrolidone-1-ylmethyl)itaconate
4-methyl 1-[3-(2-pyrrolidone-1-yl)propyl]itaconate
4-ethyl 1-[2-(2-pyrrolidone-1-yl) ethyl]itaconate
4-propyl 1-[2-(2-pyrrolidone-1-yl)ethyl]itaconate

EXAMPLE 4

Synthesis of 4-(2-phenylethyl) 1-[2-(2-pyrrolidone-1-yl)ethyl)itaconate (4-PePyEI)

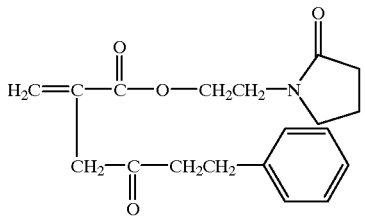

(1) Itaconic anhydride (11.2 g) and 2-phenylethanol (12.2 g) were added to benzene (100 ml) and the mixture was stirred at 60° C. for 48 hours. After the reaction solution was cooled, petroleum ether was added thereto. The deposited solid was filtered off and recrystallized from a mixed solution of benzene and petroleum ether to obtain 4-(2-phenylethyl)itaconate (12.3 g).

(2) To a methylene chloride (100 ml) solution of 4-(2-phenylethyl)itaconate (11.7 g) obtained above, thionyl chloride (8.3 g) was added and the mixture was vigorously stirred. The reaction solution was refluxed for six hours and then concentrated under reduced pressure to obtain crude 4-(2-phenylethyl)itaconyl chloride.

(3) To a benzene (100 ml) solution of crude 4-(2-phenylethyl)itaconyl chloride obtained above and 1-(2-hydroxyethyl)-2-pyrrolidone (6.5 g), a methylene chloride (20 ml) solution of triethylamine (5.1 g) was added dropwise with stirring under ice cooling. After the reaction solution was stirred at room temperature overnight, the precipitate was filtered out. The filtrate was concentrated under reduced pressure and the resulting oily substance was purified by subjecting to silica gel chromatography to obtain 9.0 g of the desired 4-(2-phenylethyl) 1-[2-(2-pyrrolidone-1-yl)ethyl] itaconate (4-PEPyEI).

$^1$H-NMR (δ, ppm, CDCl$_3$): 7.29–7.19 (m, 5H), 6.32 (s, 1H), 5.70 (s, 1H), 4.29 (m, 4H), 3.56 (t, 2H), 3.43 (t, 2H), 3.32 (s, 2H), 2.93 (t, 2H), 2.37 (t, 2H), 2.01 (m, 2H).

In the same manner as in Example 4, the following compounds can be obtained.

4-(2-phenylethyl) 1-(2-pyrrolidone-1-ylmethyl)itaconate (4-PEPyMI)

4-(2-phenylethyl) 1-[3-(2-pyrrolidone-1-yl)propyl] itaconate (4-PEPyPI)

4-phenylmethyl 1-[2-(2-pyrrolidone-1-yl)ethyl]itaconate (4-PMPyMI)

$^1$H-NMR (δ, ppm, CDCl$_3$); 7.36 (m, 5H), 6.34 (s, 1H), 5.74 (s, 1H), 5.14 (s, 2H), 4.25 (t, 2H), 3.52 (t, 2H), 3.40 (st, 4H), 2.36 (t, 2H), 1.99 (m, 2H).

4-(3-phenylpropyl) 1-[2-(2-pyrrolidone-1-yl)ethyl] itaconate (4-PPrPyMI )

4-1-butyl) 1-[2-(2-pyrrolidone-1-yl)ethyl]itaconate (4-BuPyEI)

$^1$H-NMR (δ, ppm, CDCl$_3$): 6.33 (s, 1H), 5.75 (s, 1H), 4.31 (t, 2H), 4.10 (t, 2H), 3.60 (t, 2H), 3.48 (t, 2H), 3.34 (s, 2H), 2.39 (t, 2H), 2.04 (m, 2H), 1.61 (m, 2H), 1.37 (m, 2H), 0.93 (t, 3H).

4-(2-propyl) 1-[2-(2-pyrrolidone-1-yl)ethyl]itaconate (4-PrPyEI)

$^1$H-NMR (δ, ppm, CDCl$_3$): 6.30 (s, 1H), 5.71 (s, 1H), 4.99 (m, 1H), 4.28 (t, 2H), 3.57 (t, 2H), 3.46 (t, 2H), 3.28 (s, 2H), 2.37 (t, 2H), 2.04 (m, 2H), 1.22 (d, 6H). EXAMPLE 5

Another Synthesis of 1-methyl 4-[2-(2-pyrrolidone-1-yl)ethyl]itaconate (MPyEI)

(1) To a methanol (200 ml) solution of itaconic acid (100 g), concentrated sulfuric acid (10 ml) was added and the mixture was refluxed for six hours. The reaction solution was poured into water (500 ml) and extracted with chloroform. The organic layer was dried over anhydrous sodium sulfate and concentrated under reduced pressure, and then the resulting oily substance was distilled under reduced pressure to obtain dimethyl itaconate (85 g, 60–65° C./2 mmHg).

(2) Dimethyl itaconate (20 g) obtained above was dissolved in formic acid (80 ml) and, after adding p-toluenesulfonic acid (10 g) thereto, the mixture was heated at 100° C. for 10 minutes. The reaction solution was poured into iced water (200 ml) and extracted with methylene chloride. The organic layer was dried over anhydrous sodium sulfate and concentrated under reduced pressure, and then the resulting oily substance was distilled under reduced pressure to obtain 1-methyl itaconate (7.3 g, 80–88° C./0.1 mmHg).

(3) 1-Methyl itaconate (32 g) obtained by the above method was dissolved in ether (23 ml) and, after adding thionyl chloride (23 ml) thereto, the mixture was refluxed for 15 minutes. The reaction solution was concentrated under reduced pressure and the resulting oily substance was distilled under reduced pressure to obtain 1-methyl itaconyl chloride (27 g, 68–69° C./2–3 mmHg).

(4) To a benzene (50 ml) solution of 1-(2-hydroxyethyl)-2-pyrrolidone (12.9 g) and triethylamine (10.1 g), 1-methyl itaconyl chloride (16.3 g) obtained above was added dropwise with stirring vigorously. After the reaction solution was allowed to stand at room temperature overnight, the precipitate was filtered out. The filtrate was washed in turn with 3% hydrochloric acid, an aqueous saturated sodium carbonate solution and a saturated sodium chloride aqueous solution. The organic layer was dried over anhydrous sodium sulfate and then concentrated under reduced pressure. The resulting oily substance was distilled under reduced pressure to obtain 4 g of the desired 1-methyl 4-[2-(2-pyrrolidone-1-yl)ethyl]itaconate (MPyEI).

The physical properties were the same as those obtained in Example 2.

EXAMPLE 6

Synthesis of Copolymer and Production of Sheet Made of Copolymer

Synthesis of copolymer (HEMA-PyEI-MMA) of 2-hydroxyethyl methacrylate (HEMA), 4-[2-(2-pyrrolidone-1-yl)ethyl]itaconate (PyEI) and methyl methacrylate (MMA) and production of sheet made of copolymer A solution prepared by mixing HEMA, PyEI and MMA in a ratio of 70/20/10 (w/w) and further adding 0.2% by weight of potassium persulfate and 10% by weight of water was interposed between two glass plates (6 cm×5 cm, those treated with a silicone sealing agent) fixed with a clamp while maintaining at a distance of 0.5 or 0.1 mm using a spacer, radically polymerized at 60° C. for 22 hours and then post-treated at 90° C. for two hours, thus completing the polymerization. The resulting sheet was separated from the glass plates and then the unreacted monomer was removed by dipping in purified water to obtain the desired copolymer sheet. The distance between two glass plates optionally selected.

In the same manner as in Example 6, the following copolymers and sheets made of the copolymers are obtained. HEMA-MPyEI-MMA, HEMA-4-MPyEI-MMA, HEMA-4-PEPyEI-MMA, HEMA-PyEI-MA, HEMA-MPyEI-MA, HEMA-4-MPyEI-MA, HEMA-4-PEPyEI-MA, HEA-PyEI-MMA, HEA-MPyEI-MMA, HEA-4-MPyEI-MMA, HEA-4-PEPyEI-MMA.

The above abbreviations show the following compounds (the same rule applies correspondingly to the following).

HEMA: 2-hydroxyethyl methacrylate
HEA: 2-hydroxyethyl acrylate
PyEI: 4-[2-(2-pyrrolidone-1-yl)ethyl]itaconate
MPyEI: 1-methyl 4-[2-(2-pyrrolidone-1-yl)ethyl] itaconate
4-MPyEI: 4-methyl 1-[2-(2-pyrrolidone-1-yl)ethyl] itaconate
4-PEPyEI: 4-(2-phenylethyl) 1-[2-(2-pyrrolidone-1-yl) ethyl]itaconate
MMA: methyl methacrylate
MA: methyl acrylate These copolymers and sheets thereof can also be made by using the method of Example 7 below.

Physiochemical properties of a typical example of the sheet of the copolymer made by the method of Example 6 are shown in Table 1.

TABLE 1

| Copolymer | Water content % | Refractive index | Tensile strength wet | Tensile strength dry | Recovering speed |
|---|---|---|---|---|---|
| HEMA-PyEI-MMA | 30 | 1.46 | 118.7 | — | yes |

The physiochemical properties shown in Table 1 were measured in the following procedures.

Water content: After a copolymer sheet cut into a disc form was dipped in water (0° C., 2 or more days) thereby to allow the water content to come to equilibrium, water on the surface was wiped out and the weight was measured and the resulting weight is referred to as $W_1$. The sample was dehydrated at 60° C. under reduced pressure for 48 hours and the weight in the dry state was measured and the resulting weight is referred to as $W_2$.

The water content was calculated by the formula: $(W_1-W_2)/W_1$.

Refractive Index: It was measured by using an Abbe refractometer.

Tensile strength: it was measured at a tensile rate of 12 cm/min by using a YQ-Z-7 measuring apparatus. It is represented with psi. The term "wet" means the state where the sheet is swollen with water thereby to allow the water content to come to equilibrium, while the term "dry" means the state where the sheet is prepared.

Recovering speed: The sheet was swollen with water thereby to allow the water content to come to equilibrium and cut into pieces in size of 3.0×3.0 cm and, after folding with forceps, the time required to recover the original state was measured. The applicable time is about 3 to 6 seconds with 2 seconds variation amplitude, and as long as the time is within a range from 3 to 6 seconds, it is referred to an "yes".

EXAMPLE 7

Synthesis of Copolymer (HEMA-PyEI-MMA) by Photopolymerization and Production of Sheet Made of Copolymer A solution prepared by mixing HEMA, PyEI and MMA in a ratio of 70/20/10 (w/w) and further adding 0.2% by weight of benzophenone (or 4-methacryloyloxy-2-hydroxybenzophenone) and 0.4% by weight of N,N-dimethylaminoethyl methacrylate was interposed between two glass plates (6 cm×5 cm, those treated with a silicone sealing agent) fixed with a clamp while maintaining at a distance of 0.5 or 0.1 mm using a spacer, and then photopolymerized by irradiating with ultraviolet light for 48 hours using an 80 W mercury lamp. The resulting sheet was separated from the glass plates and then the unreacted monomer was removed by dipping in purified water to obtain the desired copolymer sheet. The distance between two glass plates is optionally selected.

EXAMPLE 8

Synthesis of Crosslinked Copolymer and Production of Sheet Made of Copolymer

In the same manner as in Example 6. except that 1.0% by weight of ethylene glycol bismethacrylate (EGMA) was added to the mixture before subjecting to the radical polymerization, an intermolecular-crosslinked copolymer and a sheet made of the copolymer are obtained.

In place of EGMA, other bismethacrylate such as diethylene glycol bismethacrylate (DEGMA), and bisacrylamide such as N,N'-methylenebisacrylamide can also be used as the crosslinking agent. The amount of the crosslinking agent can be optionally selected.

EXAMPLE 9

Synthesis of Copolymer Containing Ultraviolet Absorber and Production of Sheet Made of Copolymer In the same manner as in Example 6, except that 0.8–1.5% by weight of 4-methacryloxy-2-hydroxybenzophenone (MAHBP) was added to the mixture before subjecting to the radical polymerization, a copolymer containing an ultraviolet absorber in a chemically bonded form and a sheet made of the copolymer are obtained.

EXAMPLE 10

Surface Treatment of Sheet With Polysaccharides

The copolymer sheet produced in Example 6 is dipped in an aqueous heparin solution (5%) for 24 hours and then exposed to an air for 1 hour. The resulting sheet is dipped in a sodium carbonate buffer solution (pH 11) containing divinyl sulfone (0.1%) at 40° C. for two hours, washed with a phosphate buffer solution and then washed sufficiently with water, thereby making it possible to obtain a sheet in the state where heparin and a hydroxy group are covalently bonded.

The same sheet can also be obtained by using sodium hyaluronate in place of heparin as polysaccharides.

The present invention provides a novel itaconic acid derivative, which is useful as a constituting component of a polymer, and also provides a raw material of intraocular lens formed from a copolymer containing the novel itaconic acid derivative as a constituting component, particularly foldable intraocular lens.

Advantages for use as the raw material of foldable IOL produced by forming from the copolymer containing the novel itaconic acid derivative as the constituting component are summarized below.

(1) It exhibits readily recovering from the state of being folded.
(2) It exhibits good refractive Index.
(3) It is excellent in physical strength (tensile strength).
(4) Desired properties can be obtained by changing composition ratio of each constituent monomers.
(5) Even if forceps are used in operation, marks would not remain and the surface is not impaired.
(6) Even if it is irradiated with laser beam, transparency could be maintained without causing opaque.
(7) Even if it is irradiated with laser beam, deformation or cracking would not occur.
(8) It can be hydrated after producing a copolymer because it has a hydroxy group in a molecule.
(9) The surface of copolymers could easily be treated with polysaccharide, and the copolymers could be combined with polysaccharide in covalent bond state, so it is hardly to be isolated from each other.
(10) Intermolecular crosslinking can be easily conducted.

What is claimed is:

1. An itaconic acid derivative represented by the following formula [1] or [2]:

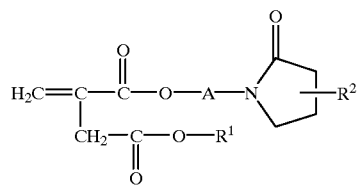

[1]

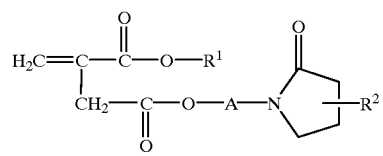

[2]

wherein $R^1$ represents hydrogen atom, lower alkyl group or phenyl lower alkyl group, and phenyl ring of the phenyl lower alkyl group is unsubstituted or substituted by lower alkyl group(s); $R^2$ represents hydrogen atom or lower alkyl group; and "A" represents lower alkylene group or a salt thereof.

2. The compound according to claim 1, wherein $R^1$ is hydrogen atom, methyl group, propyl group, butyl group, phenylmethyl group or phenylethyl group.

3. The compound according to claim 1, wherein $R^2$ is hydrogen atom.

4. The compound according to claim 1, wherein "A" is —$(CH_2)_2$—.

5. The compound according to claim 1, wherein $R^1$ is hydrogen atom, methyl group, propyl group, butyl group, phenylmethyl group or phenylethyl group, $R^2$ is hydrogen atom, and "A" is —$(CH_2)_2$—.

6. A process for producing a copolymer comprising copolymerizing (i) a monomer of the formula (7)

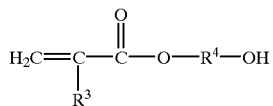

(7)

wherein $R^3$ represents a hydrogen atom or a lower alkyl group, $R^4$ represents an unsubstituted lower alkylene group, a lower alkylene group substituted by at least one hydroxy group or a lower alkylene group having at least one oxygen atom in the alkylene chain with (ii) a monomer of the formula (1) or the formula (2)

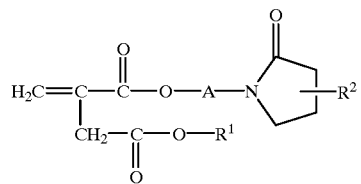

(1)

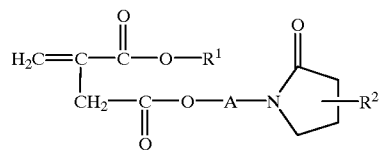

(2)

wherein $R^1$ represents a hydrogen atom, lower alkyl group or a phenyl lower alkyl group, wherein the phenyl ring of the phenyl lower group is unsubstituted or substituted with at least one lower alkyl group, $R^2$ represents a hydrogen atom or a lower alkyl group, and A represents a lower alkylene group; and with (iii) a monomer of the formula (8)

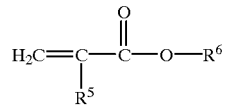

(8)

wherein $R^5$ represents a hydrogen atom or a lower alkyl group and $R^6$ represents a lower alkyl group.

7. A copolymer comprising constituent units represented by (i) a unit comprising the following formula (3):

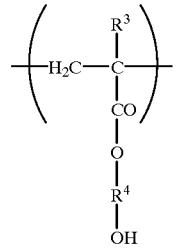

(3)

wherein $R^3$ represents a hydrogen atom or a lower alkyl group, $R^4$ represents an unsubstituted lower alkylene group, a lower alkylene group substituted by at least one hydroxy group, or a lower alkylene group having at least one oxygen atom in the alkylene chain; (ii) a unit comprising the following formulas (4) or (5):

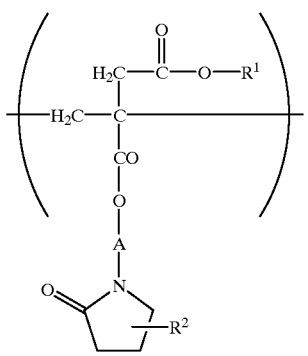

(4)

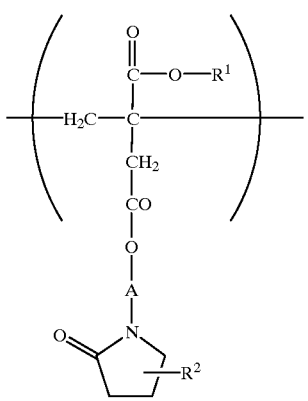

(5)

wherein $R^1$ represents a hydrogen atom, a lower alkyl group or a phenyl lower alkyl group, wherein the phenyl ring of the phenyl lower alkyl group is unsubstituted or substituted by at least one lower alkyl group, $R^2$ represents a hydrogen atom or a lower alkyl group and A represents a lower alkylene group; and (iii) a unit comprising the following formula (6):

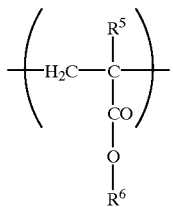

(6)

wherein $R^5$ represents a hydrogen atom or a lower alkyl group and $R^6$ represents a lower alkyl group, wherein a weight ratio of the unit comprising formula (3) is 60 to 80, a weight ratio of the unit comprising formulas (4) or (5) is 10 to 30, and a weight ratio of the unit comprising formula (6) is 5 to 20.

8. A copolymer obtained by copolymerizing monomers represented by (i) a monomer of the following formula (7):

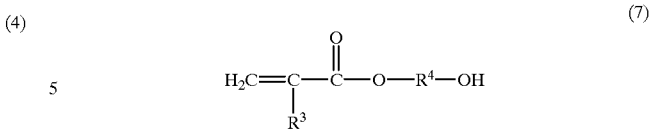

(7)

wherein $R^3$ represents a hydrogen atom or a lower alkyl group, $R^4$ represents an unsubstituted lower alkylene group, a lower alkylene group substituted by at least one hydroxy group or a lower alkylene group having at least one oxygen atom in the alkylene chain; (ii) a monomer of the following formula (1) or formula (2):

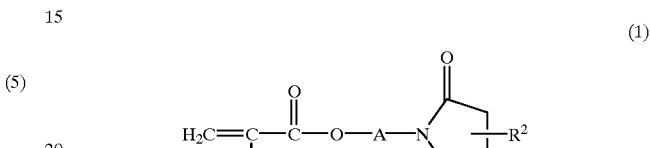

(1)

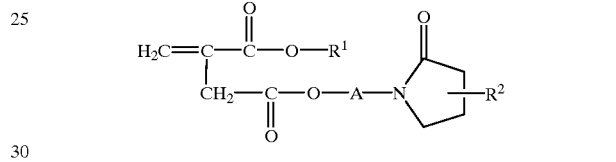

(2)

wherein $R^1$ represents a hydrogen atom, a lower alkyl group or a phenyl lower alkyl group, wherein the phenyl ring of the phenyl lower alkyl group is unsubstituted or substituted by at least one lower alkyl group, $R^2$ represents a hydrogen atom or a lower alkyl group and A represents a lower alkylene group; and (iii) a monomer of the following formula (8):

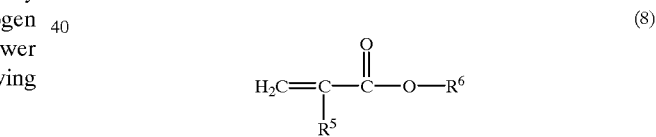

(8)

wherein $R^5$ represents a hydrogen atom or a lower alkyl group and $R^6$ represents a lower alkyl group.

9. The copolymer according to claim 7, wherein the molecular weight is from 10,000 to 100,000.

10. The copolymer according to claim 7, wherein $R^3$ is hydrogen atom or methyl group and $R^4$ is —$(CH_2)_2$—.

11. The copolymer according to claim 7, wherein $R^1$ in hydrogen atom, methyl group, propyl group, butyl group, phenylmethyl group or phenylethyl group, $R^2$ is hydrogen atom, and "A" is —$(CH_2)_2$—.

12. The copolymer according to claim 7, wherein $R^5$ is hydrogen atom or methyl group and $R^6$ is methyl group.

13. The copolymer according to claim 7, wherein $R^3$ is hydrogen atom or methyl group, $R^4$ is —$(CH_2)_2$—, $R^1$ is hydrogen atom, methyl group, propyl group, butyl group, phenylmethyl group or phenylethyl group, $R^2$ is hydrogen atom, "A" is —$(CH_2)_2$—, $R^5$ is hydrogen atom or methyl group, and $R^6$ is methyl group.

14. The copolymer according to claim 7, wherein the weight ratio of the constituent unit [3] is from 65 to 75, that of the constituent unit [4] or [5] is from 15 to 25, and that of the constituent unit [6] is from 5 to 15.

15. The copolymer according to claim 7, which is crosslinked with a bisacrylate or bisacrylamide crosslinking agent.

16. The copolymer according to claim 7, which contains an ultraviolet absorber.

17. The copolymer according to claim 7, which is surface-treated with a polysaccharide.

18. An intraocular lens produced by forming from the copolymer of claim 7.

19. A foldable intraocular lens produced by forming from the copolymer of claim 7.

20. A foldable intraocular lens produced by forming from the copolymer of claim 7, the copolymer containing an ultraviolet absorber, the surface of which is surface-treated with polysaccharide.

21. The copolymer according to claim 15, which contains an ultraviolet absorber.

22. The copolymer according to claim 15, which is surface-treated with a polysaccharide.

23. The copolymer according to claim 16, which is surface-treated with a polysaccharide.

24. The copolymer according to claim 21, which is surface-treated with a polysaccharide.

25. An intraocular lens produced by forming from the copolymer of claim 15.

26. An intraocular lens produced by forming from the copolymer of claim 16.

27. An intraocular lens produced by forming from the copolymer of claim 17.

28. An intraocular lens produced by forming from the copolymer of claim 21.

29. An intraocular lens produced by forming from the copolymer of claim 22.

30. An intraocular lens produced by forming from the copolymer of claim 23.

31. An intraocular lens produced by forming from the copolymer of claim 24.

32. A foldable intraocular lens produced by forming from the copolymer of claim 15.

33. A foldable intraocular lens produced by forming from the copolymer of claim 16.

34. A foldable intraocular lens produced by forming from the copolymer of claim 17.

35. A foldable intraocular lens produced by forming from the copolymer of claim 21.

36. A foldable intraocular lens produced by forming from the copolymer of claim 22.

37. A foldable intraocular lens produced by forming from the copolymer of claim 23.

38. A foldable intraocular lens produced by forming from the copolymer of claim 24.

39. A foldable intraocular lens produced by forming from the copolymer of claim 15, the copolymer containing an ultraviolet absorber, the surface of which is surface-treated with a polysaccharide.

* * * * *